United States Patent [19]

Mathies et al.

[11] Patent Number: 5,091,652
[45] Date of Patent: Feb. 25, 1992

[54] LASER EXCITED CONFOCAL MICROSCOPE FLUORESCENCE SCANNER AND METHOD

[75] Inventors: Richard A. Mathies; Konan Peck, both of Contra Costa, Calif.

[73] Assignee: The Regents of the University of California, Oakland, Calif.

[21] Appl. No.: 531,900

[22] Filed: Jun. 1, 1990

Related U.S. Application Data

[63] Continuation-in-part of Ser. No. 463,757, Jan. 12, 1990.

[51] Int. Cl.$^5$ .......................................... G01N 21/64
[52] U.S. Cl. ........................ 250/458.1; 250/459.1; 250/461.1; 250/461.2
[58] Field of Search ............... 250/234, 461.2, 461.1, 250/459.1, 458.1

[56] References Cited

U.S. PATENT DOCUMENTS

| 4,087,685 | 5/1978 | Froot | 250/302 |
|---|---|---|---|
| 4,284,897 | 8/1981 | Sawamura et al. | 250/461.1 |
| 4,354,114 | 10/1982 | Karnaukhov et al. | 250/458.1 |
| 4,734,578 | 3/1988 | Horikawa | 250/234 |
| 4,791,310 | 12/1988 | Honig et al. | 250/458.1 |
| 4,893,008 | 1/1990 | Horikawa | 250/234 |
| 5,022,757 | 6/1991 | Modell | 356/318 |

FOREIGN PATENT DOCUMENTS

WO86/05587 9/1986 World Int. Prop. O. ....... 250/461.1

OTHER PUBLICATIONS

Mathies, R. A. and Stryer, L. (1986), *Applications of Fluorescence in the Biomedical Sciences*, Eds. Taylor, D. L., Waggoner, A.SA., Lanni, F. Murphy, R. F., and Birge, R. (Alan R. Liss, Inc., New York) pp. 129–140.
Nguyen, D. C.; Keller R. A.; Jett, J. H.; Martin, J. C. (1987), *Detection of Single Molecules of Phycoerythrin in Hydrodynamically Focused Flows by Laser-Induced Fluorescence*, Anal. Chem. 59, 2158–2161.
Peck, K.; Stryer, L.; Glazer, A. N.; Mathies, R. A. (1989) *Single molecule fluorescence detection: Autocorrelation criterion and experimental realization with phycoerythrin* Proc. Natl. Acad. Sci. U.S.A., 86, 4087–4091.
Mathies, R. A.; Peck, K.; Stryer, L. (1990), *Optimization of High-sensitivity Fluorescence Detection*, submitted for publication.
Glaser, A. N.; Peck, K.; Mathies, R. A. (1990) *A stable double-stranded DNA—ethidium homodimer complex: Application to picogram fluorescence detection of DNA in agarose gels*, submitted for publication, Proc. Nat. Acad. Sci. U.S.A.
Ansorge, W.; Rosenthal, A.; Sproat, B.; Schwager, C.; Stegemann, J.; & Voss, H. (1988) *Non-radioactive automated sequencing of oligonucleotides by chemical degradation*, Nucleic Acids Research vol. 16, 2203–2207.
Smith, L. M.; Sanders, J. Z.; Kaiser, R. J.; Hughes, P.; Dodd, C.; Connell, C. R.; Heiner, C.; Kent, S. B. H. & Hood, L. E. (1986), *Fluorescence detection in automated DNA sequence analysis*, Nature, vol. 321, 674–679.
Sanger, F.; Nicklen, S.; & Coulson, A. R. (1977), DNA sequencing with chain-terminating inhibitors, Proc. Natl. Acad. Sci., vol. 74, No. 12, pp. 5463–5467.

*Primary Examiner*—Constantine Hannaher
*Attorney, Agent, or Firm*—Flehr, Hohbach, Test, Albritton & Herbert

[57] ABSTRACT

A fluorescent scanner for scanning the fluorescence from a fluorescence labeled separated sample on a sample carrier including a confocal microscope for illuminating a predetermined volume of the sample carrier and/or receiving and processing fluorescence emissions from said volume to provide a display of the separated sample.

9 Claims, 3 Drawing Sheets

LASER EXCITED CONFOCAL MICROSCOPE FLUORESCENCE SCANNER AND METHOD

This invention was made with United States Government support under Department of Energy Grant No. DE-FG03-88ER60706 and National Science Foundation Grant No. BBS 8720382. The Government has certain rights in this invention.

This is a continuation-in-part of co-pending application Ser. No. 463,757 filed Jan. 12, 1990.

BRIEF DESCRIPTION OF THE INVENTION

This invention relates generally to a fluorescence scanner and more particularly to a laser excited fluorescence gel scanner employing a confocal microscopic detection system.

BACKGROUND OF THE INVENTION

There is a great deal of interest in the development of automated DNA mapping and sequencing methodologies which is particularly important, in view of the recent interest in sequencing the human genome. The successful completion of this ambitious project will require improved automation. Sequence data are presently being added to data banks at a rate of $10^6$ bases/year but the human genome contains $3 \times 10^9$ base pairs.

The detection system presently used by most workers in DNA sequencing or mapping involves using radioisotope labeled DNA. The radioactive slab gels in which the DNA fragments have been separated are placed against an x-ray film for overnight exposure of the film. After the exposure and development of the x-ray film, the sequence or size of the DNA separated fragments are read directly from the images on the film.

The autoradiographic detection method described above is not only slow but also requires handling and disposal of hazardous radioactive materials. The reason autoradiography is still so widely used is because it uniquely provides the necessary sensitivity.

There has been great interest in automating the sequence determination procedures using recent advances in optical, electronic and computer technology. Autoradiographic films can now be digitized by a scanning transmission densitometer or video cameras and the digitized images can be computer processed to determine DNA sequences. These digitizing and automated sequence determination systems use autoradiography as the primary detection method.

In 1986, L. M. Smith, J. Z. Sanders, R. J. Kaiser, P. Hughes, C. Dodd, C. R. Connell, C. Heiner, S. B. H. Kent and L. E. Hood, *Nature*, vol. 321, pp. 674-679, developed a method for detecting fluorescently labeled DNA on gels which they believe is capable of sequencing ~15,000 base pairs per day. They state that one of the three areas needing development is "increasing the detection sensitivity of the system thereby allowing less material to be used per reaction which in turn allows the use of thinner gels having higher resolution." An apparatus developed by W. Ansorge, A. Rosenthal, B. Sproat, C. Schwager, J. Stegemann, and H. Voss, *Nuc. Acids Res.*, vol. 16, pp. 2203-2207 (1988), using a slightly different protocol, was able to sequence 500 base pairs in 5 hours with a sensitivity per band of $10^{-18}$ mole or $6 \times 10^5$ molecules. An analogous approach with similar capabilities was developed by J. M. Prober, G. L. Trainor, R. J. Dam, F. W. Hobbs, C. W. Robertson, R. J. Zagursky, A. J. Cocuzza, M. A. Jensen and K. Baumeister, *Science*, vol. 238, pp. 336-341 (1987).

The development of a high sensitivity detection system would obviously be very important. If very small amounts of fluorescence labeled DNA can be detected on gels, then less labeled DNA is required and the thickness of the gel can be reduced. A thinner gel will have higher resolution so it will not have to be run out as far to resolve the bands. This could result in a major saving in time. Also, the available fluorescence DNA sequencing systems require a detection system that is dedicated to the electrophoresis system during the entire approximate 10 hour run. The detection system would be more efficiently used if it detected the gels off-line from the electrophoresis. This could also result in a major saving of time and increase in throughput.

OBJECTS AND SUMMARY OF THE INVENTION

It is an object of this invention to provide a high sensitivity fluorescence detection system.

It is another object of the invention to provide a detection system with improved light collection.

It is another object of the invention to detect fluorescence emission from nucleic acids, proteins, etc., while rejecting unwanted background emission.

It is another object of the invention to choose the intensity of excitation according to the absorption coefficients and emission life time of the fluorescent molecule to give the optimum fluorescence emission with minimal background emission.

It is a further object of the invention to choose the illumination time so that it is less than the photodestruction time of the fluorescent probe to achieve a high signal-to-noise ratio.

The foregoing and other objects of the invention are achieved by a fluorescence scanner including means for applying excitation light to a medium which carries a fluorescently labeled sample to cause fluorescently labeled sample such as nucleic acids, proteins, etc. to fluoresce and for collecting the fluorescent emission from said labeled sample at a selected volume of said medium while rejecting background and scattered light through confocal spatial filtering of the detected image.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the invention as defined by the appended claims.

Increasing the fluorescence emission rate from a sample above that from the background depends on the ability to focus the excitation light to a very small spot or volume, and to gather the light from the spot or volume while rejecting background and scattered light. In fluorescence spectroscopy, it is difficult to illuminate a large area uniformly or to focus the light to a small spot with conventional light sources such as arc lamps. When mapping nucleic acids or their derivatives they are either separated by polyacrylamide or agarose gel or other gel like separation matrices with thickness from 100 $\mu$m to several millimeters. To detect nucleic acids in the gel directly by fluorescence emission, one must get rid of or reduce the scattered light from the surface of the gel, scattered light from the substrates, and background emission from the substrates.

In the present invention, a confocal microscope forms an illuminated volume in the gel. The light comprises a polarized laser beam oriented so that the background scattering can be minimized as much as possible by the polarization characteristics of the scattered light. An oil immersion objective may be used to match the refractive index of the gel and the objective lens of the optical microscope so as to reduce the scattering. It is to be understood that an air gapped objective lens may also be employed. A confocal optical arrangement is used to reject stray scattering and emission from unwanted regions of the gel or sample carrier. Dichroic beam splitters may be used in the optical system to reject the scattered light by its spectral characteristics. A spatial filter or beam stop can be used to filter out background and scattered light.

Figure 1:
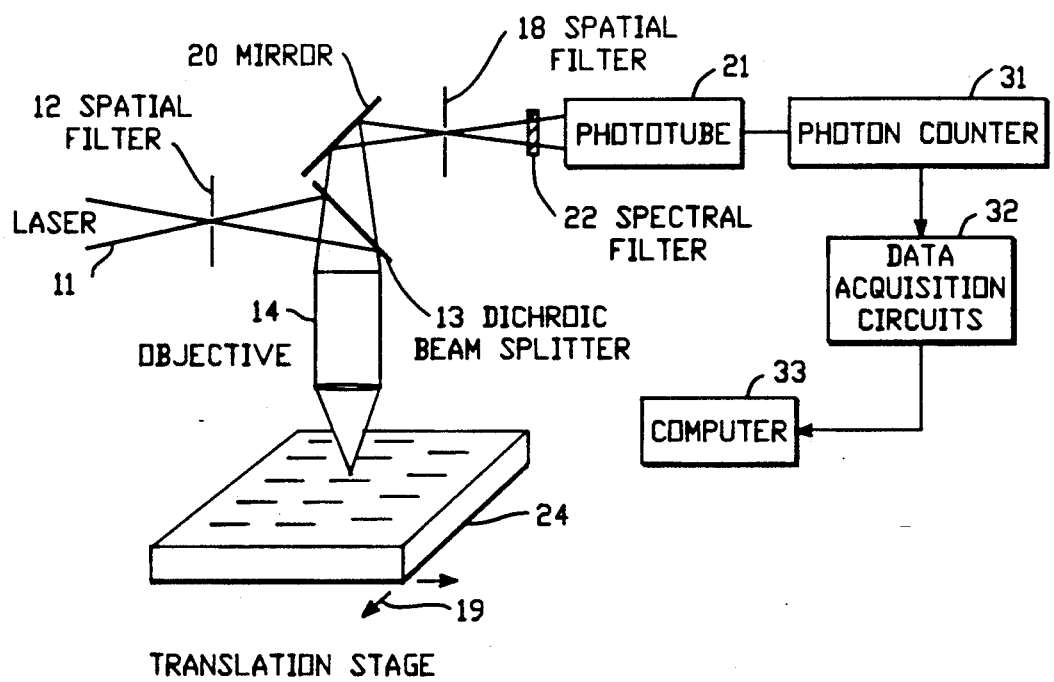
FIG. 1 shows a laser excited fluorescence gel confocal microscope scanner in accordance with one embodiment of the invention.
Figure 2:
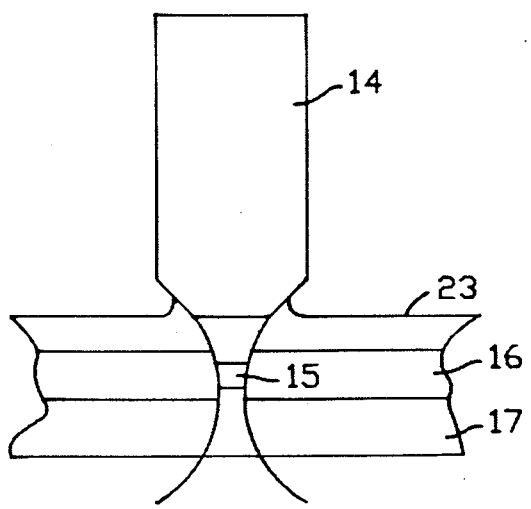
FIG. 2 is a schematic enlarged view of an objective lens assembly, the gel, gel support, gel objective interface and the volume from which fluorescence is gathered.

Referring to FIG. 1, a laser excited confocal microscope scanner is illustrated. A laser (not shown) is used as the excitation source. The laser beam 11 is first collimated and focused onto an spatial filter 12 by an 160~mm lens (not shown). After passing through spatial filter 12, the laser beam is reflected by dichroic beam splitter 13 through a 100×, N.A. 1.3 oil immersion objective 14 such as a Rolyn Optics 80.3610 10×, NA 1.3. The dichroic beam splitter reflects light at the wavelength of the excitation laser beam, but transmits fluorescence light, which is Stoke's shifted to longer wavelengths by the fluorescent sample. The objective 14 serves both as focusing lens and collection lens with very high collection efficiency. The position of the probe, volume 15, in the gel 16 supported by plate 17, FIG. 2, can be scanned either by translating the objective and the spatial filter 18 or by translating the sample holder as shown by the arrows 19. The depth of the probe column is adjusted by moving the same elements up and down. The fluorescence emission with Stoke's shifted wavelength is collected by the objective 14 and passed through the dichroic beam splitter 13 which passes Stoke's shifted emission. This reduces scattering because it will not pass scattered light at the laser wavelength.

The light is reflected to spatial filter or image stop 18 by a second dichroic beam splitter 20. The spatial filter 18 spatially filters the emitted light and passes it to the phototube detector 21 while rejecting stray, background and scattered light from the various surfaces. The second dichroic beam splitter 20 reflects only the Stoke's shifted fluorescence and lets the scattered light pass through thus providing a second rejection of the background light. It also rejects scattered or reflected light because its polarization direction is such as to pass the reflected and scattered polarized light. The emitted light is detected by a phototransducer such as a phototube 21.

The use of 160 mm focusing lens, illumination stop or spatial filter 12, and image stop or spatial filter 18 at 160 mm away from the objective lens gives this detection system a confocal arrangement which allows depth profiling of the gel. The depth of view of the detection system with 100× objective is estimated to be on the order of micrometers. By using this confocal arrangement, one can selectively probe a DNA sample volume 15 in the gel. The scattering from the surfaces of the gel is rejected by the image stop or pinhole 18. Also, the scattering and fluorescence background from the substrates will be rejected by the spatial filter. The fluorescence photons can be either directly detected by the transducer 21 or be passed through a bandpass filter 22 to further reject background emissions before detection by the detector 21.

The sample is preferably separated by electrophoresis on a slab gel. For an immersion objective the slab gel is covered with nonfluorescent immersion oil 23, FIG. 2 right after electrophoresis to prevent it from drying and cracking. The gel is then placed on a computer controlled DC servo motor driven XY translation stage 24 to translate or scan the sample gel past the focused laser volume 15.

Figure 3:
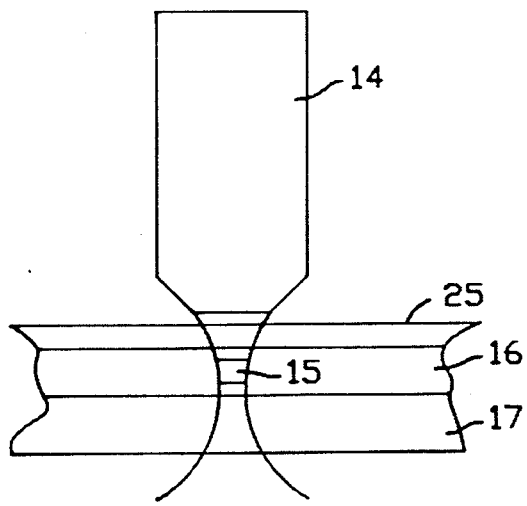
FIG. 3 is a schematic enlarged view of another assembly of the type shown in FIG. 2.

FIG. 3 shows a non-immersion objective lens assembly in which the gel is covered by a thin glass plate 25 which prevents drying out of the gel.

A microcomputer with an analog-to-digital board or a frame grabber board is used to digitize data from the data acquisition circuit. The data acquisition circuit 24, FIG. 4 consists of a preamplifier 26 to amplify signal from photomultiplier tube, a discriminator 27 to reject thermal noises and other low amplitude electronic noises introduced by the photomultiplier and the preamplifier. A frequency to voltage converter 28 converts counts to analog signal for processing with analog-to-digital converter 29. This photon counting and analog signal conversion method has the fast and relatively easy processing advantage of analog circuits while it also has the digital photon counting sensitivity that DC measurements lack. A more inexpensive version would simply use a photomultiplier tube, preamplifier and analog-to-digital converter as in FIG. 5.

The data can also be processed digitally, in which mode, the counts from the photodetector 21 are processed by a timer/counter 31, FIG. 1, or frequency counter or multichannel scaler directly without the frequency to voltage converter and the digital-to-analog converter. Data acquisition circuit 32 provides data to a computer 33. The computer controls the XY translation stage 24 and displays acquired image in real time.

Figure 6:
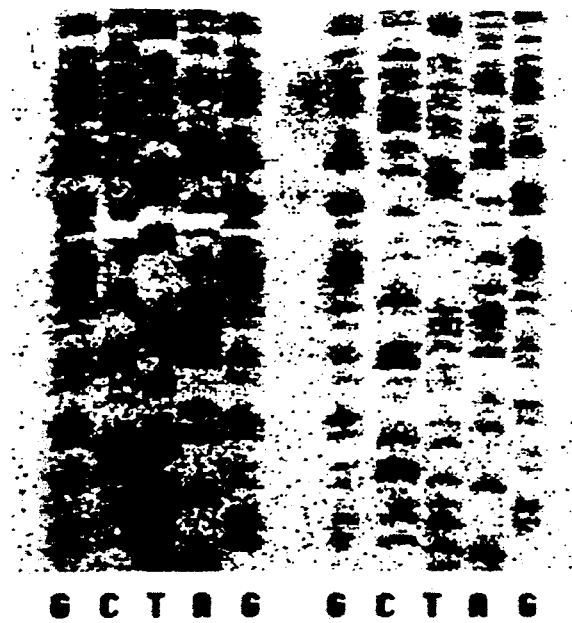
FIG. 6 shows a typical image formed by the gel scanner of the present invention.

FIG. 6 shows an example of a DNA sequencing gel image obtained by this invention. Each band in the image represents one DNA fragment of a particular length. The averaged quantity per band in this image is about $10^5$ molecules. The fluorescence images are contrast-stretched with a histogram equalization method to enhance the images. The direct imaging of DNA or RNA in the gel by fluorescence emission has much better linearity than densitometric scanning of autoradiographic films which usually has logarithmic response.

Figure 7:
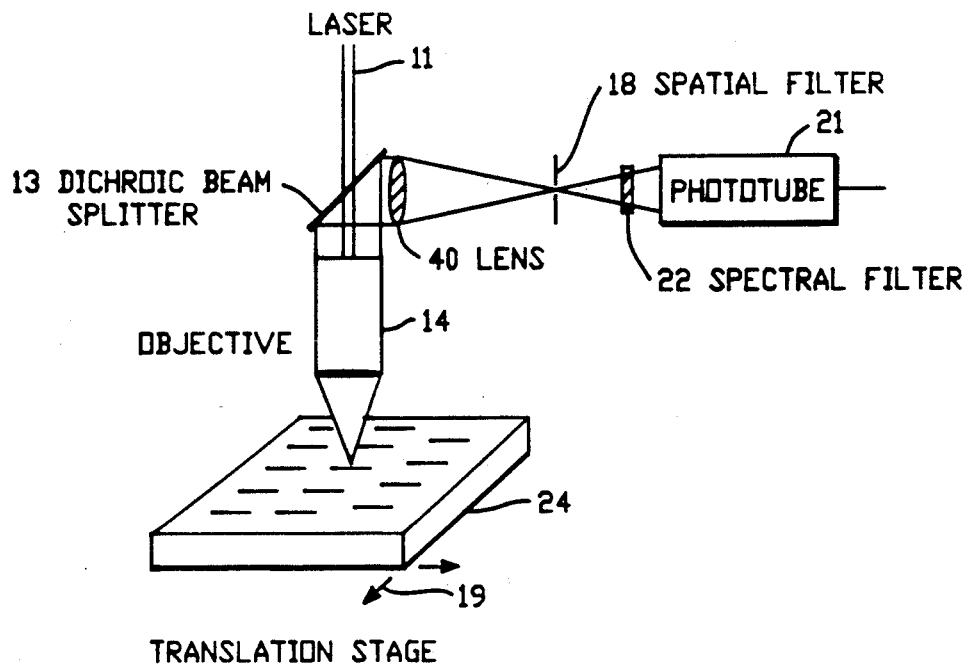
FIG. 7 shows another laser excited fluorescence gel scanner in accordance with the present invention.
Figure 8:
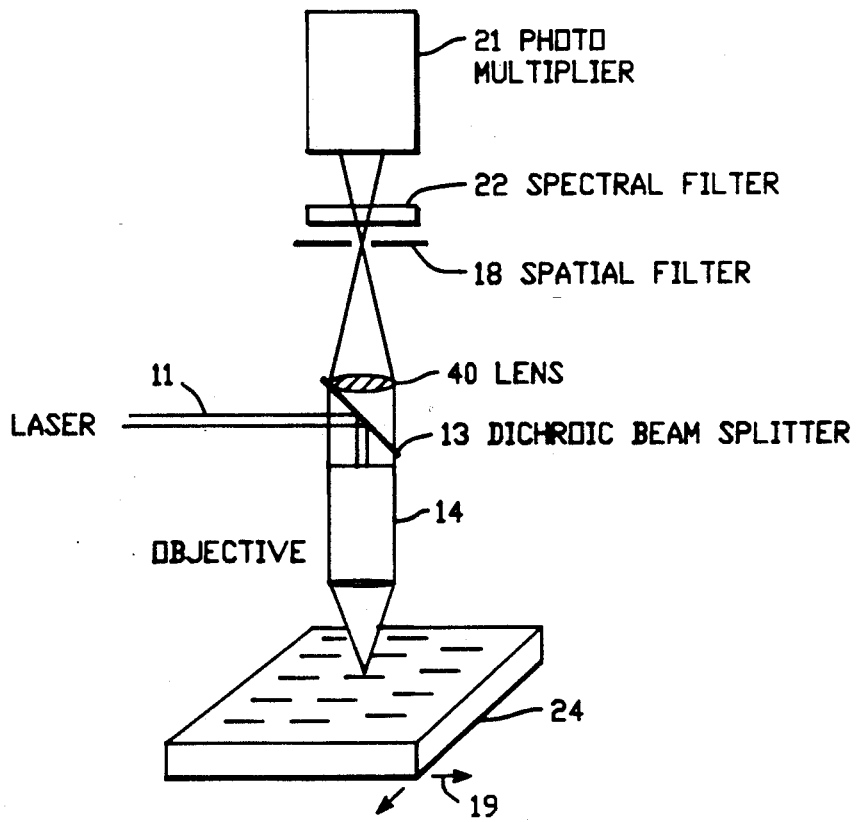
FIG. 8 shows still another embodiment of a fluorescence gel scanner in accordance with another embodiment of the present invention.

FIGS. 7 and 8 show other embodiments of fluorescence gel scanners incorporating the present invention. Reference numbers have been applied to parts previously described. In each instance a collimated laser beam is directly applied through the lens assembly to a small volume of the gel. The fluorescence from the sample at the small volume is collected by the objective and focused through a spatial filter by a lens (40) to a detector (photomultiplier tube). In other respects, the scanner operates as described above. The location of the sensed volume within the gel may be selected by moving the gel, or by moving the lens assembly and spatial filter.

It is important to point out that these configurations are fundamentally better than an imaging charge coupled device (CCD) or charge injection device (CID) coupled to a fluorescence microscope. A fluorescence microscope is designed to image a very tiny area; however, the entire field is illuminated so that the incident intensity in any given small area is low. Furthermore, to image a large area like a electrophoresis slab gel, one has to use a lens that can project the whole image onto the camera at one time. This means using a large F-number lens with low collection efficiency. Despite the high quantum efficiency of charge coupled devices, the detection system as a whole is not as sensitive as a photon counting photomultiplier tube in this kind of application.

It is also worth pointing out that this invention has better sensitivity over the fluorescence detection system described by Smith et al., *Nature*, (1986) simply due to the better collection efficiency offered by the microscope objective lens and the background rejection methods intrinsic to the confocal spatial filtering of the detected light.

In a preliminary experiment the detection limits of this invention for DNA sequencing gel reached about $1 \times 10^5$ molecules per band on the average with a 250 $\mu$m thick gel and 3 mm wide sample well. Although the on-line detection method described by Smith, et al. (1986) has advantages, the off-line detection method taught in this invention doesn't require a laser and detection system dedicated to every electrophoresis system. This allows several gels being run simultaneously to have higher throughput and is more economical.

In summary, the laser excited confocal fluorescence scanning system taught herein is a very sensitive method for detecting DNA and RNA in gels. This invention employs a confocal microscope with a high numerical aperture objective to achieve the highest collection efficiency possible. The invention teaches polarization, spectral filtering, spatial filtering and refractive index matching principles to effectively reduce background in order to obtain optimum detection limits. The electronic gating of noises by photon counting with frequency to voltage conversion provides further improvement in signal-to-noise. The translation of the gel across the laser beam provides a means to image a large electrophoresis gel with high sensitivity and spatial resolution. The ultimate spatial resolution in this fluorescence imaging system is determined by the spot size of the laser beam which can be as small as 1-2 $\mu$m in diameter using the optical elements described in this invention. The combination of high spatial resolution and low detection limits of this fluorescence imaging system means that very low detection limits can be easily achieved which approach the limits of autoradiography.

As an improved instrument for fluorescence detection and imaging of electrophoresis gels, this invention should be of interest to biological or biochemical researchers, particularly those working in DNA sequencing and mapping. This invention can detect DNA samples that cannot be detected by conventional fluorescence detection methods, and it provides a faster and safer way to do DNA sequencing without handling radioactive materials. It is apparent that the invention may be used to detect and image fluorescent labeled molecules, proteins, virus and bacteria, etc., which are electrophoretically or otherwise separated on a variety of carriers such as membranes, filter paper, petrie dishes, glass substrates, etc.

The foregoing descriptions of specific embodiments of this invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best use the invention and various embodiments with various modifications as are suited to the particular use contemplated. It is intended that the scope of the invention be defined by the claims appended hereto and their equivalents.

We claim:

1. An improved gel scanner comprising
   means for supporting a gel to be scanned,
   means for forming a light beam of predetermined wavelength;
   a dichroic beam splitter for receiving and directing said beam toward a supported gel to be scanned;
   an objective lens for receiving said beam and focusing the beam in a selected volume of gel to cause fluorescence emission of light at a different wavelength and collecting the emitted light from samples in said selected volume and directing the emitted light to said dichroic beam splitter which passes said emitted light of different wavelengths and reflects light at said predetermined wavelength;
   a spatial filter for receiving and passing the emitted light from said volume while rejecting background and scattered light;
   means for providing relative movement between said focused beam and the gel being scanned,
   means for detecting said passed, emitted light and providing output signals, and
   means for processing said signals to provide an image of the fluorescence from the gel.

2. The method of detecting fluorescence from DNA fragments on a gel which comprises exciting a predetermined volume of said gel with light energy of predetermined wavelength focused therein by an objective lens to cause said fragments to fluoresce at a different wavelength;

collecting the fluorescently emitted light from said predetermined volume with said objective lens;

spectrally and spatially filtering said fluorescently emitted light energy of different wavelength to reject light at said predetermined and other wavelengths; and applying the filtered light energy to a detector to generate an output signal representative of the fluorescence from said fragments.

3. The method of claim 2 in which the excited volume is scanned across the gel to obtain emission from adjacent volumes to provide an output signal for each of said volumes, and processing the output signals to provide an image of the fluorescence from said fragments.

4. A scanner for scanning a gel to detect fluorescence from fluorescence labeled separated sample components comprising means for supporting a gel to be scanned, means for applying excitation light at a predetermined wavelength to a volume in the gel to cause labeled, separated sample components to fluoresce at a different wavelength, and for collecting the fluorescence emitted light from said sample at said different wavelength from said volume and reject the first wavelength;

means for moving said excitation light and gel relative to one another to scan the gel;

at least one spectral filter for receiving the collected emitted light and passing light at said different wavelength while rejecting light at said predetermined wavelength;

a spatial filter for receiving the emitted light and passing light from said sample volume while rejecting background and scattered light;

detecting means for receiving said collective fluorescently emitted light passed by said spectral and spatial filters and providing output signals, and means for receiving and processing said signals to provide an image of the labeled separated sample components.

5. A scanner as in claim 4 including a laser for supplying said excitation light.

6. An improved scanner as in claim 5 including a spatial filter for receiving said light beam and transmitting light to said dichroic beam splitter.

7. An improved scanner for detecting fluorescence from a fluorescence labeled sample material carried by a sample carrier comprising means for forming a light beam having a predetermined wavelength;

a dichroic beam splitter for receiving said light beam and directing it towards an objective lens which receives said beam and focuses the beam at a spot on the sample carrier whereby to cause the sample material to fluoresce at a selected volume and for collecting the fluorescently emitted light from said selected volume and directing the emitted light to said dichroic beam splitter, said fluorescent light being at a second wavelength and said dichroic beam splitter serving to pass the second wavelength;

a spatial filter for receiving light at said second wavelength and passing light emitted from said selected volume;

a spectral filter for further filtering said light and passing light at said second wavelength;

means for moving the light beam and sample carrier relative to one another to scan the sample carrier, means for detecting the passed, emitted light of said second wavelength and providing output signals representative of the intensity of said detected light, and means for receiving and processing said signals to provide an image of the fluorescence of said samples.

8. An improved fluorescence scanner as in claim 7 in which the carrier is a gel and the sample is a nucleic acid or derivative thereof.

9. An improved gel scanner comprising means for supporting a gel to be scanned, means for forming a light beam of predetermined wavelength;

a dichroic beam splitter for receiving and transmitting said beam toward a supported gel to be scanned;

an objective lens for receiving said beam and focusing the beam in a selected volume of gel to cause fluorescence emission of light at a different wavelength and collecting the emitted light from samples in said selected volume and directing the emitted light to said dichroic beam splitter which reflects said emitted light of different wavelengths and rejects light at said predetermined wavelength;

a spatial filter for receiving and passing the emitted light from said volume while rejecting background and scattered light;

means for providing relative movement between said focused beam and the gel to be scanned, means for detecting said passed, emitted light and providing output signals, and means for processing said signals to provide an image of the fluorescence from the gel.

* * * * *

UNITED STATES PATENT AND TRADEMARK OFFICE
CERTIFICATE OF CORRECTION

PATENT NO. : 5,091,652

DATED : February 25, 1992

INVENTOR(S) : R.A. Mathies et al.

Figure 4:
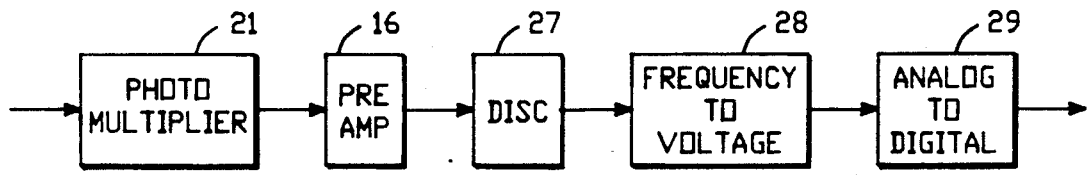
FIG. 4 is a block diagram of a suitable data acquisition circuit.
Figure 5:
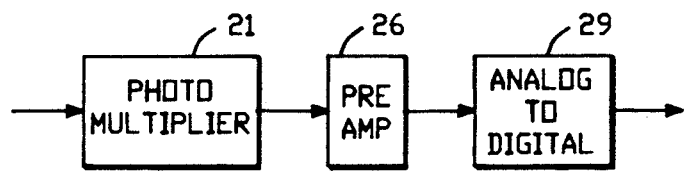
FIG. 5 is a block diagram of another data acquisition circuit.

It is certified that error appears in the above-identified patent and that said Letters Patent is hereby corrected as shown below:

In the Drawings, in Figure 4, change "16" to --26--

On the title page, under OTHER PUBLICATIONS:

At column 1, line 3, amend "A.S.A." to --A.S.--

At column 2, line 10, amend "Glaser" to --Glazer--

On the title page, In thr Abstract:

At line 1, amend "fluorescent" to fluorescence--;

At line 2, amend "Fluorescence" labeled separated sample" to --fluorescently labeled sample separated--

At line 6, before "separated" insert --location and amount of the--

Column 1, line 30, delete "radioactive"

Column 1, line 31, after "the" and before "DNA" insert --radioactive--

Column 1, line 34, amend "DNA separated" to read --separated DNA--

Column 2, line 5, amend "fluorescence" to read -- fluorescently--

Column 3, line 52, amend "an spatial" to --a spatial--

Column 3, line 56, amend "80.3610 10" to --80.3610 100--

UNITED STATES PATENT AND TRADEMARK OFFICE
CERTIFICATE OF CORRECTION

PATENT NO. : 5,091,652
DATED : February 25, 1992
INVENTOR(S) : R.A. Mathies et al.

It is certified that error appears in the above-identified patent and that said Letters Patent is hereby corrected as shown below:

Column 4, line 24, after "with" insert --a--

Column 4, line 48, delete "24"

Column 4, line 50, after "from" insert --the--

Column 4, line 60, after "preamplifier" insert --26--

Column 4, line 61, after "converter" insert --29--

Column 5, line 1, after "displays" insert --the--

Column 5, line 34, amend "a electrophoresis" to --an electrophoresis--

Column 7, lines 30-31, amend " and eject the first wavelength" to read --and rejecting light at the predetermined wavelength--

Column 7, lines 51-52, amend "light beam and transmitting light to said dichroic beam splitter" to read --excitation light and transmitting said excitation light to said means for applying excitation light--

Signed and Sealed this

Twelfth Day of October, 1993

Attest:

BRUCE LEHMAN

*Attesting Officer*  *Commissioner of Patents and Trademarks*